United States Patent
Khan

(10) Patent No.: US 6,955,169 B2
(45) Date of Patent: Oct. 18, 2005

(54) INHALER DEVICE

(76) Inventor: Khaja H. Khan, 497 Gregory Ave., Apt. 2C, Glendale Heights, IL (US) 60139

( * ) Notice: Subject to any disclaimer, the term of this patent is extended or adjusted under 35 U.S.C. 154(b) by 177 days.

(21) Appl. No.: 10/185,474

(22) Filed: Jun. 27, 2002

(65) Prior Publication Data

US 2004/0000307 A1 Jan. 1, 2004

(51) Int. Cl.$^7$ .......................... A61M 11/00; G01L 19/12
(52) U.S. Cl. ............................ 128/200.22; 128/200.23; 222/51; 116/228; 116/268; 116/272; 239/74
(58) Field of Search ....................... 128/200.23, 200.14, 128/203.23, 200.22; 600/529, 540, 538, 539; 482/13; 222/51, 155, 157; 116/222, 228, 268, 272, 273; 239/71, 74

(56) References Cited

U.S. PATENT DOCUMENTS

| | | | | |
|---|---|---|---|---|
| 2,267,009 A | * | 12/1941 | Adolphsen et al. | .... 128/202.22 |
| 3,635,214 A | * | 1/1972 | Rand et al. | ................. 600/540 |
| 4,210,155 A | * | 7/1980 | Grimes | ....................... 600/540 |
| 4,259,951 A | * | 4/1981 | Chernack et al. | ....... 128/200.14 |
| 4,444,202 A | * | 4/1984 | Rubin et al. | ................. 600/538 |
| 5,067,707 A | * | 11/1991 | Kohnke | ....................... 482/13 |
| 5,385,140 A | | 1/1995 | Smith | |
| 5,431,154 A | * | 7/1995 | Seigel et al. | ........... 128/200.14 |
| 5,522,380 A | * | 6/1996 | Dwork | .................... 128/200.23 |
| 6,305,371 B1 | | 10/2001 | Frid et al. | |
| 6,708,688 B1 | * | 3/2004 | Rubin et al. | ........... 128/200.23 |

* cited by examiner

*Primary Examiner*—Henry Bennett
*Assistant Examiner*—Mital Patel

(57) ABSTRACT

A device used with fluid canisters comprising a transparent body allowing the viewing of movement within the body having a minor and major cavity with a float indicator and float seat within the minor cavity. An inhaler top and bottom fits each end of the body forming an airtight chamber within the major and minor cavity above the float, the top having a seat to accept a canister and a nozzle aperture to accept a nozzle of the canister oriented to release fluid from the canister into the major cavity. An inlet through the minor cavity below the seat maintains pressure equal to pressure outside of the body within the minor cavity. Inhalation through a mouthpiece and one way valve reduces pressure within the major and minor cavity above the float drawing fluid through the one way valve creating a pressure difference across the float causing it to move.

14 Claims, 1 Drawing Sheet

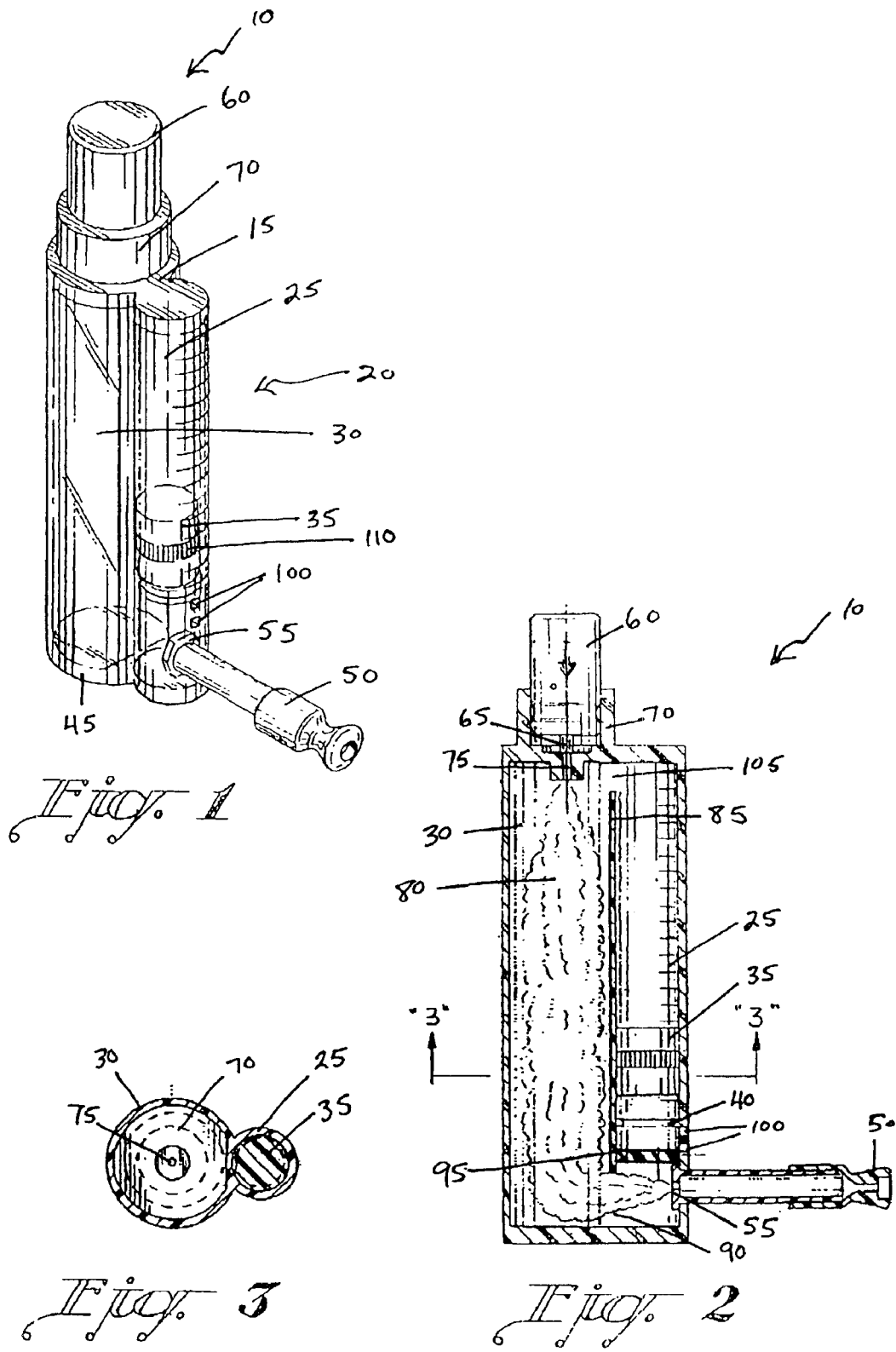

INHALER DEVICE

BACKGROUND OF THE INVENTION

1. Field of the Invention

The present invention generally relates to medicine inhalers. More specifically, the present invention relates to medicine inhalers having structure for viewing the inhalation of medicine.

2. Description of the Prior Art

Persons with respiratory ailments such as asthma or emphysema commonly use prescription drugs such as Albuterol to treat their aliment. Drugs of this type are generally made in liquid form and are stored in small medicine canisters. The medicine canisters generally have a nozzle within one end to release the liquid in the form of a mist. The mist is then inhaled into the lungs to medicate the user of the drug.

The medicine canister is typically used by placing the canister into an inhaler device that facilitates the transferal of the medicinal mist to the user's lungs. A typical inhaler device consists of a housing for receiving the canister, a seat portion with passage for directing the flow of the mist, and a mouthpiece. U.S. Pat. No. 6,305,371 issued to Frid et al. illustrates a typical inhaler device of this type. Inhaler devices of this type are commonly used by placing the mouthpiece of the inhaler device into the user's mouth and pressing down on the top of the medicine canister, actuating the nozzle portion of the canister. The medicinal mist is then released through the nozzle and into a passageway that directs the mist in the proper direction with the proper intensity.

Inhaler devices of this type do not provide the user with information about the effectiveness of a self-administered dose and coincidentally does not alert the person using the device as to whether he or she is using the inhaler device properly. Therefore, a user of this type of inhaler device has to go through a period of trial and error to arrive at a proper method of using the device so as to achieve desired results. Further, younger users may have difficulty in using an inhaler device of this type with repetitive accuracy. Therefore, a need has arisen for an inhaler device that provides the user with information about the effectiveness of their self-administered dosages.

Other devices have been designed to attempt to fulfill this need. U.S. Pat. No. 5,522,380 issued to Dwork is one of these devices. This device provides an incentive spirometer for delivering medication to patients from metered dose inhaler canisters. A ball inside the indicator tube provides the user with information as to whether or not the user is drawing upon the mouthpiece with a proper amount of force so as to draw the ball toward the top of the indicator tube. This type of information is somewhat useful in that it notifies the user whether he or she is inhaling with an amount of force that would result in lifting the ball within the indicator tube. However, this device does not provide the user with information concerning whether or not the mist delivered by the medicine canister was properly received by the user. Therefore, there is a need for an improved inhaler device that provides the user with a greater amount of information about the effectiveness of the user's efforts to properly inhale the mist dispensed by the medicine canister.

Further, the Dwork device is configured such that the medicine canister is positioned within the line of sight of the indicator tube. As a consequence, the medicine canister partial blocks the view of the indicator tube preventing the user from fully viewing the activity in the indicator tube. Therefore, there is a need for an improved inhaler device that provides the user with an unobstructed view of the activity in the inhaler device.

Even further, the Dwork device does not provide indicia of the amount of force the user is using to draw the medicinal mist into the user's lungs other than the indication that the user has inhaled with an amount of force to bring the ball within the indicator tube to stop at the top of the indicator tube. Accordingly, users who may have difficulty repeatedly drawing upon the mouthpiece with the proper amount of force, do not have a point of reference to gage their efforts. Therefore, there is still a need for an inhaler device that more readily provides the user with information regarding the amount of force that is required to inhale a proper dosage of medicinal mist.

Devices such as the aerosol inhalation device disclosed in U.S. Pat. No. 5,385,140 issued to Smith are also used in conjunction with the common inhaler device as discussed above. The aerosol inhalation device is used to provide a chamber for receiving the medicinal mist where the velocity of the mist is reduced before it is introduced into the user's mouth. The inhalation device allows the user to view the activity inside the device but does not provide the user with readily viewable indicia of the dosage progress. Therefore, there remains a need for an improved inhaler device that allows the user to readily view the progress of the user's inhalation.

SUMMARY OF THE INVENTION

An object of the claimed invention is to provide an improved inhaler device that provides the users with readily viewable feedback of the user's inhalation progress.

Another object of the claimed invention is to provide an improved inhaler device that provides an unobstructed view of the activity in the inhaler device.

A further object of the claimed invention is to provide an improved inhaler device that provides feedback to the user as to the progress of the user's inhalation.

An even further object of the claimed invention is to provide an improved inhaler device with a float indicator interacting with the inhalation of the medicinal mist to provide a user of the device with accurate, readily viewable feedback of the progress of the user's inhalation.

To achieve the foregoing and other objectives, an improved inhaler device is provided. The device comprises a transparent inhaler body having a minor cavity in communication with a major cavity. A float indicator sized and shaped to moveably and sealedly fit within the minor cavity resides within the minor cavity to provide a user of the device with visual feedback as to the use of the device.

An inhaler top sized and shaped to sealedly fit a first end of the body has a seat structure sized and shaped to accept a medicine canister containing a medicinal fluid. Further, the inhaler top has a nozzle aperture sized and shaped to accept a nozzle connected to the canister oriented such that medicinal fluid released from the nozzle enters the major cavity of the body. An inhaler bottom sized and shaped to sealedly fit a second end of the body forms an airtight chamber within the major cavity and within the minor cavity above the float indicator. A float indicator seat within the minor cavity provides a seat for the float indicator while the inhaler device is not in use.

At least one inlet aperture through an outer wall of the minor cavity below the float indicator seat maintains pressure within the minor cavity below the float indicator substantially equal to ambient pressure outside of the body. The float indicator seat prevents the float indicator from obstructing the inlet aperture.

A mouth piece in communication with the interior of the body by way of a one way valve within an outer wall of the body is located such that inhalation through the mouth piece reduces the pressure within the major cavity and within the minor cavity above the float indicator. The reduction in pressure within the major cavity and minor cavity draws the medicinal fluid through the one way valve and mouthpiece and creates a pressure difference across the float indicator. The pressure difference across the float indicator causes the float indicator to move toward the inhaler top, the transparency of the body allowing visualization of the float indicator moving toward the inhaler top as the medicinal fluid moves from the major cavity and through the one way valve and mouthpiece into the user's mouth.

BRIEF DESCRIPTION OF THE DRAWINGS

FIG. 1. FIG. 1 shows a perspective view of the inhaler device.

FIG. 2. FIG. 2 shows a vertical cross section view of the inhaler device.

FIG. 3. FIG. 3 shows a horizontal cross section view of the inhaler device.

DETAILED DESCRIPTION OF THE PREFERRED EMBODIMENT

FIGS. 1–3 show an embodiment of the inhaler device 10. The inhaler device as shown in FIGS. 1–3 is used in an upright fashion to provide an unobstructed view of the activity in the inhaler device 10 during use. The inhaler device 10 generally consists of an inhaler top 15, an inhaler body 20 having a minor cavity 25 and a major cavity 30, a float indicator 35 and float indicator seat 40, an inhaler bottom 45, and a mouthpiece 50 connected to the body 20 by a one way valve 55. A medicine canister 60 can be placed in the inhaler device 10 as shown.

The medicine canister 60 as shown in FIGS. 1 and 2 is a standard canister having a nozzle 65 that dispenses the medicinal mist 80 from the medicine canister 60. The inhaler device 10 as shown in FIGS. 1–3 is designed to accept this standard sized canister 60, however it is within the scope of the invention that the inhaler device 10 could be designed to accept canisters of other sizes.

FIGS. 1 and 2 show the inhaler top 15 is generally sized and shaped to fit over an end of the inhaler body 20 and has a seat structure 70 for receiving a medicine canister containing medicine for treating respiratory ailments. The inhaler top 15 is preferably made of plastic, but may be made of other similar materials. The nozzle 65 of the medicine canister 60 fits into a channel 75 that controls the spray intensity of the mist 80 dispensed from the medicine canister 60 and directs the mist 80 within major cavity 30 of the inhaler body 20. When the user pushes against the top of the medicine canister 60, the nozzle 65 sprays the mist 80 into the inhaler body 20 through the channel 75 into the major cavity 30. The inhaler bottom 45 is generally sized and shaped to fit over an end of the inhaler body 20 to effectively enclose the major cavity 30 and minor cavity 25.

The inhaler body 20 is preferably made of transparent plastic so that a user of the inhaler device 10 may watch the movement of the fluids inside of the inhaler body 20 during use. The inhaler body 20 has a generally circular minor cavity 25 in communication with a generally circular major cavity 30. In a preferred embodiment of the claimed invention, the minor cavity is about 6.5 centimeters in diameter and the major cavity is about 13 centimeters in diameter, both having a height of about 18 centimeters. A vertical interior wall 85 between the minor cavity 25 and major cavity 30 partially separates the two cavities, terminating on either end before reaching the inhaler top 15 and inhaler bottom 45. The opening 90 near the inhaler bottom 45 allows the mist 80 to be drawn from the major cavity 30 into the lower portion of the minor cavity 25 when the user inhales upon the mouthpiece 50. A horizontal wall 95 within the minor cavity 25 prevents the mist 80 from escaping through inlets 100 within the body wall of the minor cavity 25. The opening 105 near the inhaler top 15 allows the inhalation by the user to reduce the pressure within the minor cavity 25 above the float indicator 35.

The float indicator 35 is generally shaped to fit within the minor cavity 25 of the inhaler body 20 and is sized slightly smaller than the inner dimensions of the minor cavity 25 so that the float indicator 35 may move freely within the minor cavity 25. An O-ring type gasket 110 within the side surfaces of the indicator float 35 creates a seal between the float indicator 35 and the inner walls of the minor cavity 25 to prevent fluids from moving between the float indicator 35 and the inner walls of the minor cavity 25. The seal created by the gasket 110 forms a relatively airtight chamber within the major cavity 30 and within the minor 25 cavity above the float indicator 35.

A plurality of inlet apertures 100 are located within the body wall of the minor cavity 25 allowing air from out side of the body 20 to enter into the minor cavity 25 below the float indicator 35. Ambient air entering the minor cavity 25 below the float indicator 35 maintains the pressure within the minor cavity 25 below the float indicator 35 at a pressure roughly equal to the pressure out side of the inhaler body 20. A float indicator seat 40 located within the minor cavity 25 above the inlet apertures 100 prevent the float indicator 35 from obstructing the inlet apertures 100.

A mouthpiece 50 connected to the one way valve 55 allows a user of the device 10 to inhale medicine from the medicine canister 60. The one way valve 55 used in the device 10 can be of several different designs such as the one way valve disclosed in U.S. Pat. No. 5,385,140 issued to Smith, and are commercially available from several different manufactures. A user of the device 10 places the mouthpiece 50 between the user's lips, press down on the medicine canister 60 so as to release medicine into the inhaler body 20, and draws upon the mouthpiece 50 by inhaling deeply. As the user inhales through the mouthpiece 50, the mist 80 is drawn through the one way valve 55 and mouthpiece 50 into the mouth of the user where the medicine is drawn into the lungs.

To use the inhaler device 10, the user places the mouthpiece 50 between the user's lips and presses down on the medicine canister 60, releasing mist 80 into the major cavity 30 of the inhaler body 20. As the user inhales through the mouthpiece 50, a vacuum is created within the inhaler body 20. The vacuum created by the inhalation of the user draws the mist 80 from the major cavity 30 into the lower portion of the minor cavity 25, through the one way valve 55 and into the user's mouth by way of the mouthpiece 50. The transparency and length of the inhaler body 20 allows the user of the device to see the movement of the mist 80 within the inhaler body 20 so that the user of the device 10 can see the amount of mist 80 dispensed into the body 20.

As the mist 80 is drawn from the inhaler body 20, a pressure difference is created within the minor cavity 25 across the float indicator 35. The opening 105 near the inhaler top 15 allows the pressure within the minor cavity 25 above the float indicator 35 to be reduced as the pressure in the major cavity 30 is reduced. The O-ring gasket 110 about the float indicator 35 maintains the vacuum within the major cavity 30 and the upper portion of the minor cavity 25. The inlets 100 in the minor cavity 25 below the float seat 35 maintain the pressure of the lower portion of the minor cavity 25 at pressure equal to the ambient pressure outside of the device 10. The pressure difference across the float indicator 35 causes the float indicator 35 to rise within the minor cavity 25 when the user inhales upon the mouthpiece 50.

The movement of the float indicator 35 towards the inhaler top 15 provides the user of the device 10 with visual feedback as to the progress of administering the dose of medicine. This visual feedback can be used by the user of the device 10 to modify and/or monitor the user's method of self-administration of a dose thereby aiding the user to more effectively administer medicine of this type.

Although the invention has been described by reference to some embodiments it is not intended that the novel device be limited thereby, but that modifications thereof are intended to be included as falling within the broad scope and spirit of the foregoing disclosure, the following claims and the appended drawings.

I claim:

1. An inhaler device for use with a medicinal fluid canister, the device comprising:
    a transparent inhaler body having a minor cavity in communication with a major cavity and an interior wall between the major cavity and the minor cavity limiting communication between the major cavity and minor cavity to less than half of the area common between the major cavity and minor cavity;
    a float indicator sized and shaped to moveably fit within the minor cavity having a gasket about a side surface of the float indicator providing a seal between the float indicator and the inner walls of the minor cavity;
    an inhaler top sized and shaped to sealedly fit a first end of the body having a seat structure sized and shaped to accept a medicine canister containing a medicinal fluid, the inhaler top having a nozzle aperture sized and shaped to accept a nozzle connected to the canister oriented such that medicinal fluid released from the nozzle enters the major cavity of the body and a channel adjacent the nozzle aperture controlling the intensity and direction of the medicinal fluid within the major cavity;
    an inhaler bottom sized and shaped to sealedly fit a second end of the body forming an air tight chamber within the major cavity and within the minor cavity above the float indicator;
    a float indicator seat within the minor cavity, the float indicator resting upon the float indicator seat while the inhaler device is not in use;
    at least one inlet aperture allowing air from the outside of the body to enter through an outer wall of the minor cavity below the float indicator seat maintaining pressure within the minor cavity below the float indicator substantially equal to ambient pressure outside of the body, the float indicator seat preventing the float indicator from obstructing the inlet aperture; and
    a mouth piece in communication with the interior of the body by way of a one way valve within an outer wall of the body situated such that inhalation through the mouth piece reduces the pressure within the major cavity and within the minor cavity above the float indicator drawing the medicinal fluid through the one way valve and mouth piece creating a pressure difference across the float indicator causing the float indicator to move toward the inhaler top, the transparency of the body allowing visualization of the float indicator moving toward the inhaler top as the medicinal fluid moves from the major cavity and through the one way valve and mouthpiece.

2. The inhaler device of claim 1 wherein the one way valve and mouthpiece are connected to the body such that the float indicator can be readily viewed during use of the device.

3. The inhaler device of claim 2 further comprising reference indicators on an outer wall of the minor cavity of the body.

4. The inhaler device of claim 3 wherein the major cavity and the minor cavity are substantially circular in shape and a long axis of the major cavity is substantially parallel with a long axis of the minor cavity.

5. The inhaler device of claim 4 wherein the substantially circular shape of the minor cavity retains the float indicator within the minor cavity.

6. The inhaler device of claim 5 wherein a long axis of the medicinal canister is in line with the long axis of the major cavity.

7. An inhaler device for use with a medicinal fluid canister having a transparent body for visualization of medicinal fluid evacuation from the body dispensed from the canister into the body during use, the body having a movable float indicator indicating progress of the evacuation of the medicinal fluid from the body with a gasket about the float indicator creating a seal between the float indicator and inner walls of the transparent body, wherein the body has a minor cavity in communication with a major cavity, the float indicator sized and shaped to moveably and sealedly fit within the minor cavity; an inhaler top sized and shaped to sealedly fit a first end of the body having a seat structure sized and shaped to accept a medicine canister containing a medicinal fluid, the inhaler top having a nozzle aperture sized and shaped to accept a nozzle connected to the canister oriented such that the medicinal fluid released from the nozzle enters the major cavity of the body; a float indicator seat within the minor cavity, the float indicator resting upon the float indicator seat while the inhaler device is not in use; at least one inlet aperture allowing air from outside of the body to enter through an outer wall of the minor cavity below the float indicator seat maintaining pressure within the minor cavity below the float indicator substantially equal to ambient pressure outside of the body, the float indicator seat preventing the float indicator from obstructing the inlet aperture.

8. The inhaler device of claim 7 further comprising a mouth piece in communication with the interior of the body by way of a one way valve within an outer wall of the body situated such that inhalation through the mouth piece reduces the pressure within the major cavity and within the minor cavity above the float indicator drawing the medicinal fluid through the one way valve and mouth piece creating a pressure difference across the float indicator causing the float indicator to move toward the inhaler top, the transparency of the body allowing visualization of the float indicator moving toward the inhaler top as the medicinal fluid moves from the major cavity and through the one way valve and mouthpiece.

9. A method of dispensing a medicant, the method comprising:

propelling a charge of medicant into a first transparent cavity;

applying suction at the bottom of the first cavity simultaneously causing suction within a second cavity;

introducing ambient pressure into the second cavity;

sectioning the second cavity with a gasketed indicator;

utilizing the suction within the second cavity to create a pressure difference across the gasketed indicator thereby elevating the indicator thus providing a visual indication in the second cavity to gage proper inhalation of the medicant;

spacing the propulsion and suction such that movement of the medicant within the first transparent may be visualized.

10. An inhaler device for use with a medicinal fluid canister, the device comprising:

a transparent inhaler body having a minor cavity in communication with a major cavity, an outer wall of the minor cavity having reference indicators;

a float indicator sized and shaped to moveably and sealedly fit within the minor cavity having a gasket about a side surface of the float indicator providing the seal between the float indicator and the inner walls of the minor cavity;

an inhaler top sized and shaped to sealedly fit a first end of the body having a seat structure sized and shaped to accept a medicine canister containing a medicinal fluid, the inhaler top having a nozzle aperture sized and shaped to accept a nozzle connected to the canister oriented such that medicinal fluid released from the nozzle enters the major cavity of the body and a channel adjacent the nozzle aperture sized and shaped to control the intensity and direction of the medicinal fluid within the major cavity;

an inhaler bottom sized and shaped to sealedly fit a second end of the body forming an air tight chamber within the major cavity and within the minor cavity above the float indicator;

a float indicator seat within the minor cavity, the float indicator resting upon the float indicator seat while the inhaler device is not in use;

at least one inlet aperture allowing air from outside of the body to enter through an outer wall of the minor cavity below the float indicator seat maintaining pressure within the minor cavity below the float indicator substantially equal to ambient pressure outside of the body, the float indicator seat preventing the float indicator from obstructing the inlet aperture; and a mouth piece in communication with the interior of the body by way of a one way valve within an outer wall of the body situated such that the float indicator can be readily viewed during use of the device as inhalation through the mouth piece reduces the pressure within the major cavity and within the minor cavity above the float indicator drawing the medicinal fluid through the one way valve and mouth piece creating a pressure difference across the float indicator causing the float indicator to move toward the inhaler top, the transparency of the body allowing visualization of the float indicator moving toward the inhaler top as the medicinal fluid moves from the major cavity and through the one way valve and mouthpiece.

11. The device of claim 10 wherein the major cavity and the minor cavity are substantially circular in shape and a long axis of the major cavity is substantially parallel with a long axis of the minor cavity.

12. The device of claim 11 further comprising an interior wall between the major cavity and the minor cavity that limits the communication between the major cavity and minor cavity to less than half of the area common between the major cavity and the minor cavity.

13. An inhaler device for use with a medicinal fluid canister, the device comprising:

an inhaler body having a minor cavity in communication with a major cavity;

a float indicator sized and shaped to moveably fit within the minor cavity having a gasket about a side surface providing a seal between the float indicator and inner walls of the minor cavity;

a float indicator seat within the minor cavity, the float indicator resting upon the float indicator seat while the inhaler device is not in use;

at least one inlet aperture allowing air from outside of the body to enter through an outer wall of the minor cavity below the float indicator seat maintaining pressure within the minor cavity below the float indicator substantially equal to ambient pressure outside of the body;

a mouth piece in communication with the interior of the body situated such that inhalation through the mouth piece reduces pressure within the major cavity and within the minor cavity above the float creating a pressure difference across the float indicator causing the float indicator to move.

14. The device of claim 13 wherein the mouth piece is in communication with the body by way of a one way valve.

* * * * *